United States Patent
Hastings et al.

(10) Patent No.: US 6,251,061 B1
(45) Date of Patent: *Jun. 26, 2001

(54) CARDIAC ASSIST DEVICE USING FIELD CONTROLLED FLUID

(75) Inventors: Roger N. Hastings, Maple Grove; Bruce Persson, Columbia Heights; Dnyanesh Talpade; Daniel M. LaFontaine, both of Plymouth, all of MN (US)

(73) Assignee: SciMed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/149,941

(22) Filed: Sep. 9, 1998

(51) Int. Cl.[7] .............................. A61F 2/02; A61F 2/48; A61F 2/04

(52) U.S. Cl. .............................................. 600/16; 600/17

(58) Field of Search ........................................ 600/16, 17

(56) References Cited

U.S. PATENT DOCUMENTS

| 3,568,214 | * | 3/1971 | Goldschmied | 600/16 |
|---|---|---|---|---|
| 4,621,617 | | 11/1986 | Sharma | 128/1 D |
| 4,650,485 | | 3/1987 | Sala | 623/3 |
| 4,779,614 | | 10/1988 | Moise | 600/16 |
| 4,894,013 | | 1/1990 | Smith et al. | 434/268 |
| 4,895,557 | | 1/1990 | Moise et al. | 600/16 |
| 4,908,012 | | 3/1990 | Moise et al. | 600/16 |
| 5,350,413 | | 9/1994 | Miller | 607/61 |
| 5,450,853 | | 9/1995 | Hastings et al. | 128/675 |
| 5,498,228 | | 3/1996 | Royalty et al. | 600/16 |
| 5,507,629 | | 4/1996 | Jarvik | 417/423.3 |
| 5,749,839 | | 5/1998 | Kovacs | 601/153 |
| 5,762,599 | | 6/1998 | Sohn | 600/30 |
| 6,074,365 | | 6/2000 | Hähndel et al. | 604/151 |

FOREIGN PATENT DOCUMENTS

| 2 321 266 | 3/1977 | (FR) | A61F/1/22 |
|---|---|---|---|
| 2 767 565 | 2/1999 | (FR) | F04B/43/00 |
| 2 772 971 | 6/1999 | (FR) | H01F/7/06 |
| 8-087056 | 6/1993 | (JP) | F04B/45/04 |
| WO 98/17347 | 4/1998 | (WO) | A61N/1/362 |
| WO 98/30271 | 7/1998 | (WO) | A61M/29/00 |

* cited by examiner

Primary Examiner—William E. Kamm
Assistant Examiner—Carl H. Layno
(74) Attorney, Agent, or Firm—Joseph R. Kelly; Westman, Champlin & Kelly, P.A.

(57) ABSTRACT

A cardiac assist device and method of use for assisting the function of a heart. The assist device includes a compressor positioned against the epicardial wall of the heart and a field generator for driving a fluid coupled to the compressor to exert pressure on the heart. The field generator may be a magnetic field generator and the fluid coupled to the compressor may be a ferrofluid. The compressor may include two containment regions containing ferrofluid on opposite sides of the heart, and a pair of compression portions coupled to the containment regions. The filled generator may be electromagnetic which includes two electromagnets having corresponding core portions and corresponding coils. The electromagnets may be disposed with their north and south poles in alignment and separated by a gap to allow relative movement. The electromagnets may be external or internal to the body.

25 Claims, 10 Drawing Sheets

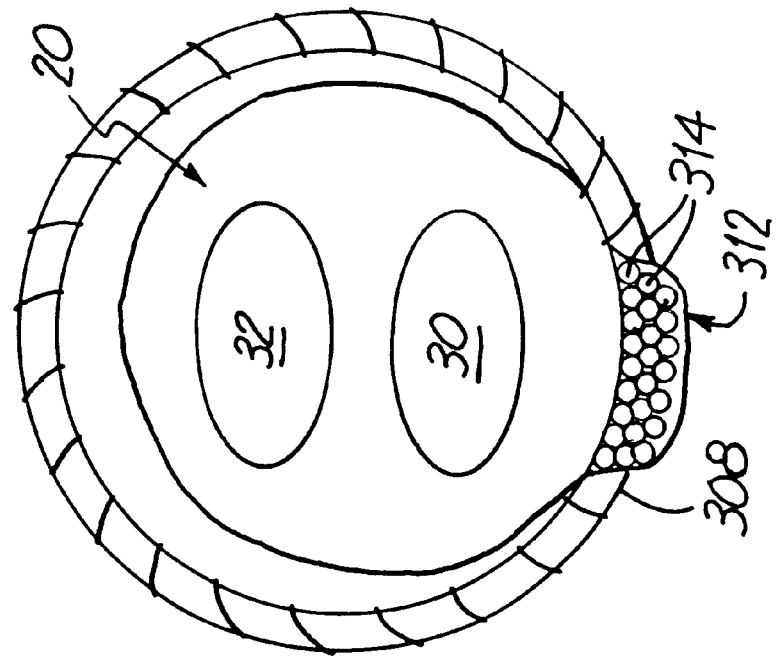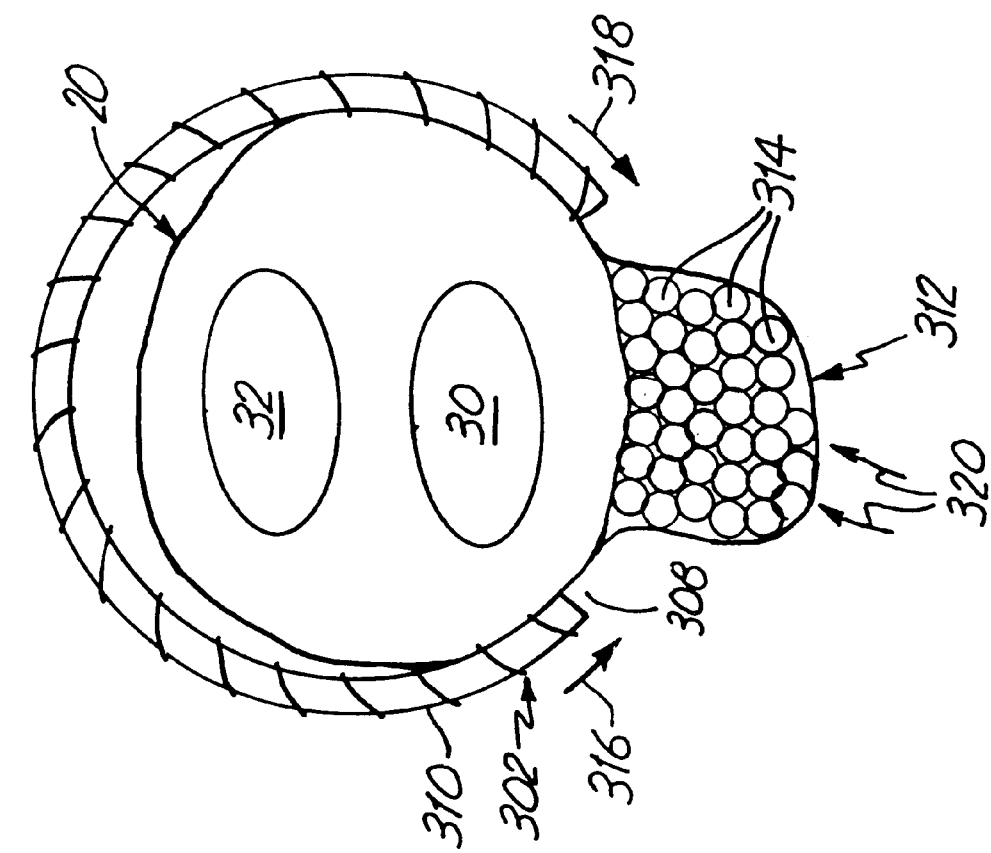

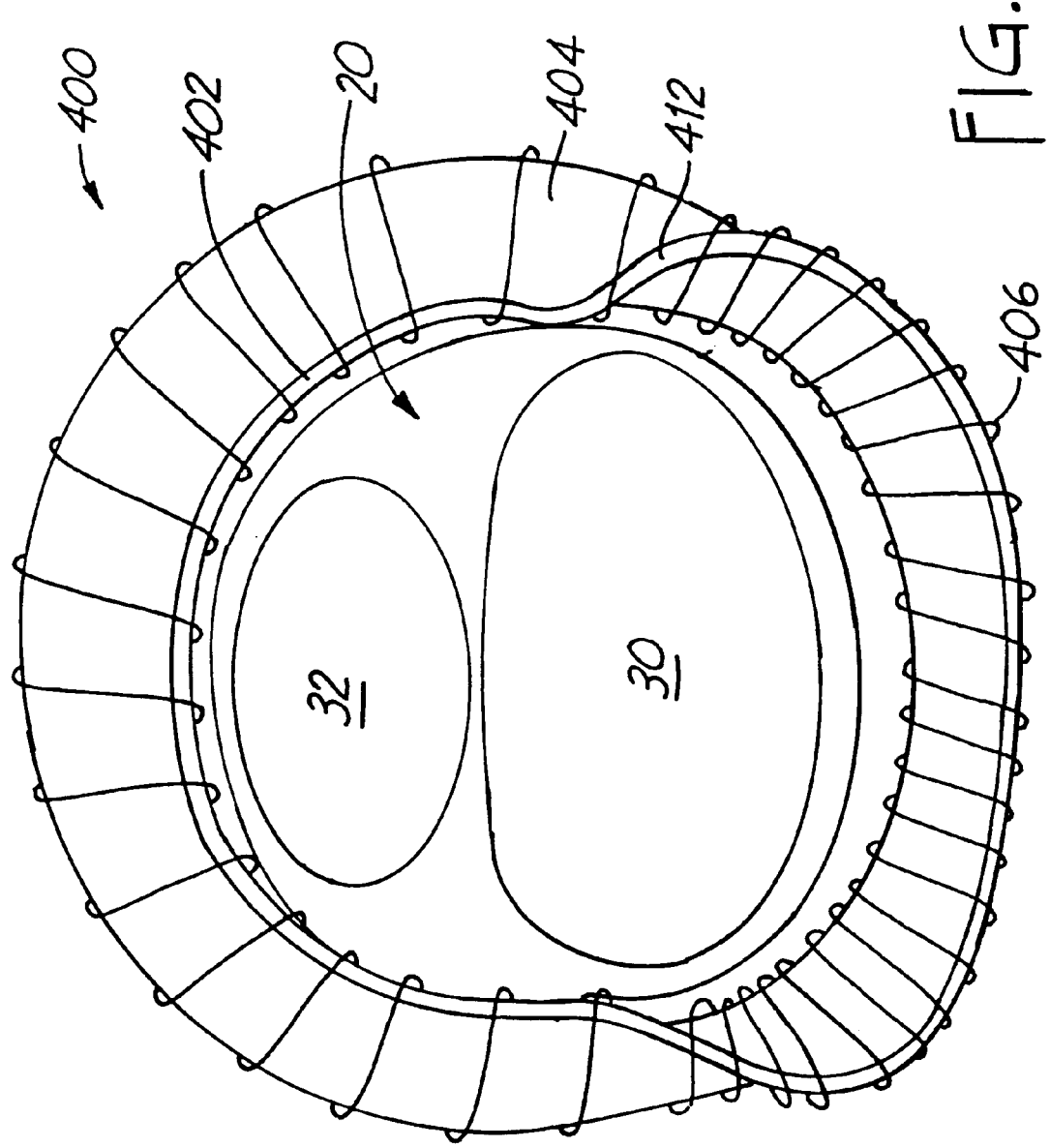

CARDIAC ASSIST DEVICE USING FIELD CONTROLLED FLUID

BACKGROUND OF THE INVENTION

The present invention deals with a ventricular assist device. More particularly, the present invention deals with cardiomyoplasty using a ferro fluid or other similar fluid.

A number of different types of coronary disease can require ventricular assist. Present ventricular assist devices (VADs) employ mechanical pumps to circulate blood through the vasculature. These pumps are typically plumbed between the apex of the left ventricle and the aortic arch (for LVADs), and provide mechanical assistance to a weak heart. These devices must be compatible with the blood, and inhibit thrombus formation, due to the intimate contact between the pump components and the blood.

Cardiomyoplasty is a form of ventricular assist which includes squeezing the heart from the epicardial surface to assist the ejection of blood from the ventricles during systole. This form of ventricular assist does not require contact with blood or surgical entry into the cardiovascular system. It has been expressed in several embodiments over the years. The first involves an approach which is drastically different from the mechanical pump approach discussed above. The approach uses a muscle in the patient's back. The muscle is detached and wrapped around the epicardium of the heart. The muscle is then trained to contract in synchrony with the ECG pulse, or other pulse (which may be generated by a pacemaker). Since the back muscle does not contact blood, many of the issues faced by conventional LVADs are avoided. However, this approach also suffers from disadvantages, because operation of the muscle tissues is poorly understood and largely uncontrolled.

A number of other methods are also taught by prior references. Some such references disclose balloons or bellows which squeeze on the exterior surface of the heart in synchrony with the ECG signal. U.S. Pat. No. 3,455,298 to Anstadt discloses an air pressure source which is used to inflate a balloon about a portion of the external surface of the heart, in order to provide a squeezing pressure on the heart.

Other references disclose similar items which are inflated using fluid inflation devices. Still other references disclose mechanical means which apply pressure radially inwardly on the epicardial surface of the heart. For instance, U.S. Pat. No. 4,621,617 to Sharma discloses an electromechanical mechanism for applying external pressure to the heart.

The air and fluid inflation devices exhibit certain advantages in that they use conformable fluids to provide an atraumatic squeezing force on the surface of the heart, as opposed to mechanical and electromechanical devices which use rigid surfaces, which contact the heart, in order to exert the squeezing force. However, one disadvantage of the fluid devices is the need for a pump which delivers fluid from a reservoir. The pump and the associated electronics is generally bulky, and can be too large and cumbersome to be implanted within the patient. Thus, such devices often require the patient to remain in bed while the device is in use.

Further, while the human muscle wrap approach does address some of these problems, it requires radical surgery plus the training of the muscle, which may not always be accomplished successfully.

SUMMARY OF THE INVENTION

The present invention is directed to a cardiac assist device for assisting the function of a heart. The assist device includes a compressor positioned against the epicardial wall of the heart and a field generator for driving a fluid coupled to the compressor to exert pressure on the heart. The pressure exerted against the heart improves heart function.

The field generator may be a magnetic field generator and the fluid coupled to the compressor may be a ferrofluid. The magnetic field generator may include an electromagnet having a core and an energizeable coil disposed thereabout. The ferrofluid may be disposed proximate a gap in the electromagnet such that the compressor exerts a force against the heart wall by generation of a magnetic field in the gap.

The compressor may include two containment regions containing ferrofluid on opposite sides of the heart, and a pair of compression portions coupled to the containment regions. The electromagnet may include two electromagnets having corresponding core portions and corresponding coils. The electromagnets may be disposed with their north and south poles in alignment and separated by a gap to allow relative movement. The electromagnets may be external or internal to the body.

BRIEF DESCRIPTION OF THE DRAWINGS

FIGS. 5A–5C illustrate an assist device in accordance with another aspect of the present invention.

FIGS. 6A–6C illustrate an assist device in accordance with another aspect of the present invention.

DETAILED DESCRIPTION OF THE PREFERRED EMBODIMENTS

Figure 1:
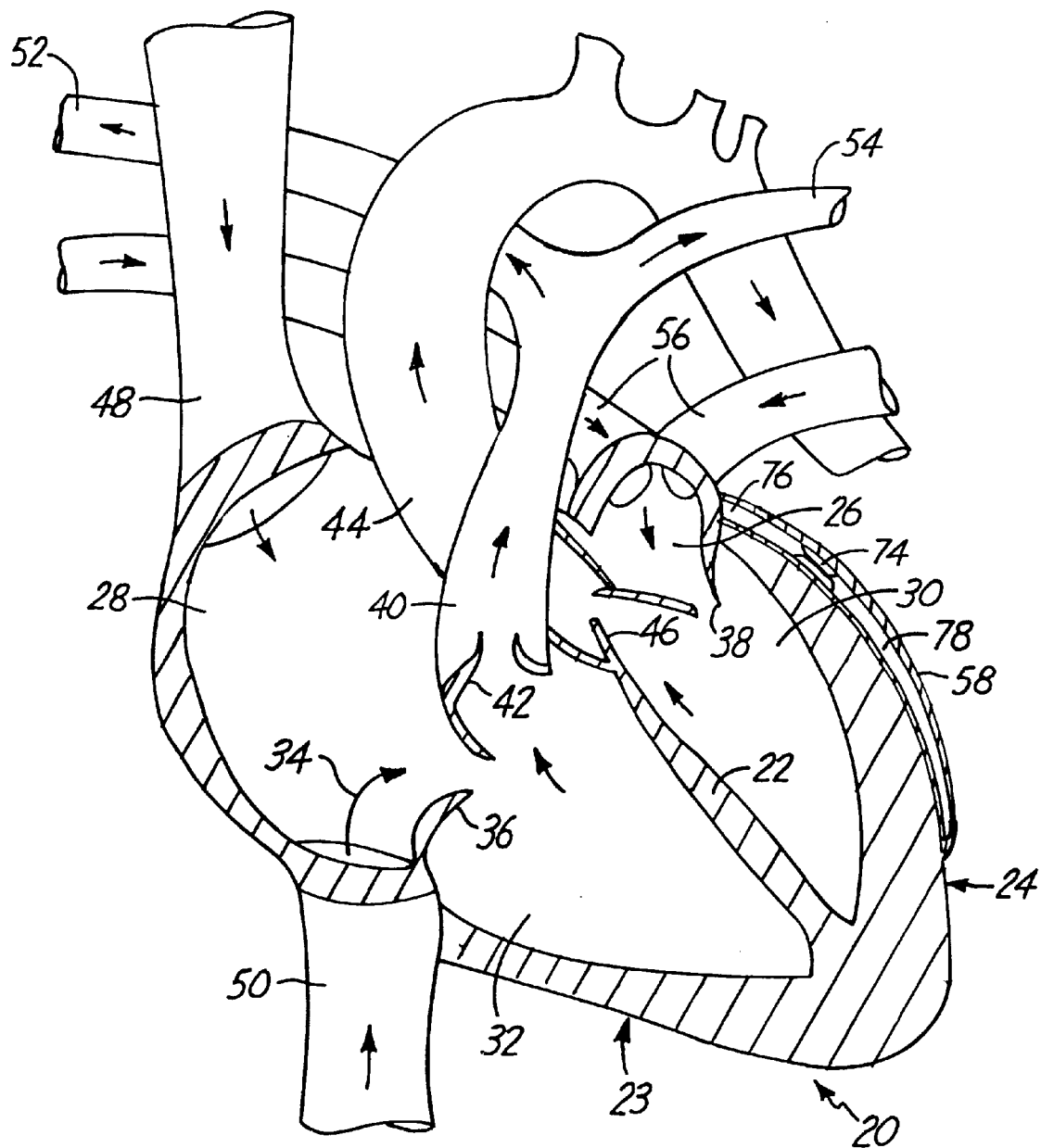
FIG. 1 illustrates a partial sectional view of a human heart and its associated proximate vascular system.

FIG. 1 illustrates a partially sectioned view of a human heart 20, and its associated vasculature. The heart 20 is subdivided by muscular septum 22 into two lateral halves, which are named respectively right 23 and left 24. A transverse constriction subdivides each half of the heart into two cavities, or chambers. The upper chambers consist of the left and right atria 26, 28 which collect blood. The lower chambers consist of the left and right ventricles 30, 32 which pump blood. The arrows 34 indicate the direction of blood flow through the heart. The chambers are defined by the epicardial wall of the heart.

The right atrium 28 communicates with the right ventricle 32 by the tricuspid valve 36. The left atrium 26 communicates with the left ventricle 30 by the mitral valve 38. The right ventricle 32 empties into the pulmonary artery 40 by way of the pulmonary valve 42. The left ventricle 30 empties into the aorta 44 by way of the aortic valve 46.

The circulation of the heart 20 consists of two components. First is the functional circulation of the heart 20, i.e., the blood flow through the heart 20 from which blood is pumped to the lungs and the body in general. Second is the coronary circulation, i.e., the blood supply to the structures and muscles of the heart 20 itself.

The functional circulation of the heart 20 pumps blood to the body in general, i.e., the systematic circulation, and to the lungs for oxygenation, i.e., the pulmonic and pulmonary circulation. The left side of the heart 24 supplies the systemic circulation. The right side 23 of the heart supplies the lungs with blood for oxygenation. Deoxygenated blood from the systematic circulation is returned to the heart 20 and is supplied to the right atrium 28 by the superior and inferior venae cavae 48, 50. The heart 20 pumps the deoxygenated blood into the lungs for oxygenation by way of the main pulmonary artery 40. The main pulmonary artery 40 separates into the right and left pulmonary arteries, 52, 54 which circulate to the right and left lungs, respectively. Oxygenated blood returns to the heart 20 at the left atrium 26 via four pulmonary veins 56 (of which two are shown). The blood then flows to the left ventricle 30 where it is pumped into the aorta 44, which supplies the body with oxygenated blood.

The functional circulation, however, does not supply blood to the heart muscle or structures. Therefore, functional circulation does not supply oxygen or nutrients to the heart 20 itself. The actual blood supply to the heart structure, i.e., the oxygen and nutrient supply, is provided by the coronary circulation of the heart, consisting of coronary arteries, indicated generally at 58, and cardiac veins. Coronary artery 58 resides closely proximate the endocardial wall of heart 24. The coronary artery 58 includes a proximal arterial bed 76 and a distal arterial bed 78 downstream from the proximal bed 76.

In order to assist the heart, the present invention provides a fluid either partially surrounding the heart, or completely surrounding the heart, wherein the fluid can be influenced by electric or magnetic fields. The fluid is located closely proximate the epicardial surface of the heart and is influenced by the application of an electric or magnetic field in order to assist the heart.

Figure 2:
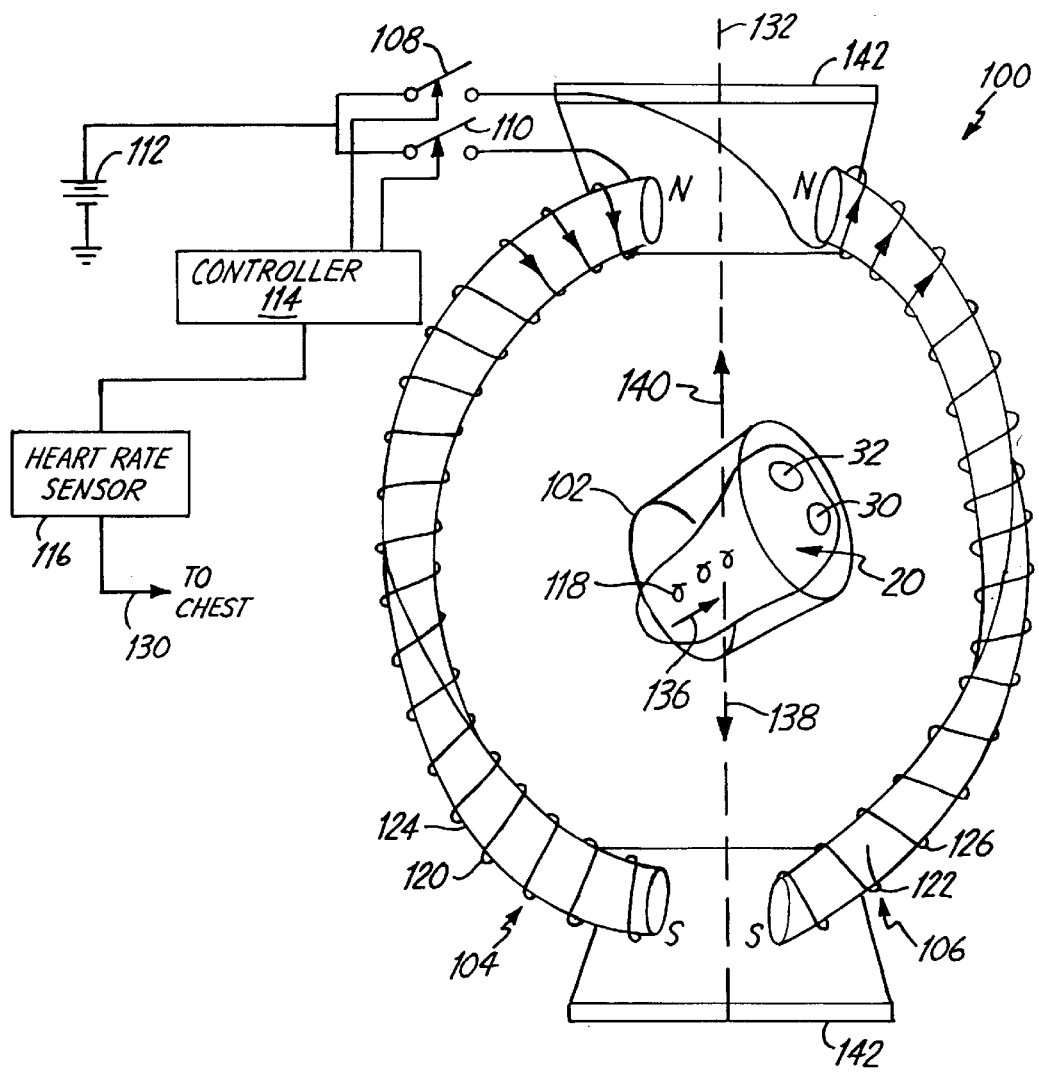
FIG. 2 is a diagrammatic illustration, in partial schematic form, of an assist device in accordance with one aspect of the present invention.

FIG. 2 is a diagram, in partial schematic form, illustrating cardiomyoplasty system 100 which is used, in accordance with one aspect of the present invention, in order to assist the heart 20. In system 100, heart 20 is illustrated surrounded by a bag 102 which is substantially, or partially, filled with a ferrofluid (shown in FIG. 3). System 100 also includes electromagnet sections 104 and 106 which are coupled, through switches 108 and 110, to a power supply 112. Switches 108 and 110 are controlled by controller 114 which, in one preferred embodiment, receives an ECG input signal from heart rate sensor or monitor 116.

In one preferred embodiment, bag 102 is formed of a non-compliant balloon material which is preferably attached to portions of the heart by sutures, indicated generally at 118. Bag 102 is filled with a ferrofluid which, in one preferred embodiment, is paramagnetic in that it becomes magnetic in the presence of an applied magnetic field. Such fluids are commercially available from Ferrof luidics Corporation, 40 Simon Street, Nashua, N.H. 03061, and Lord Corporation, 405 Gregson Drive, Cary, N.C. 27511. The fluid is preferably biocompatible and includes suspensions of small, ferromagnetic particles. In zero applied field, the fluid is non-magnetic. However, the fluid becomes magnetized when an external magnetic field is applied. The maximum magnetization which can occur in the fluid is referred to as the saturation induction, and is typically achieved in applied fields of about 1000 Oersteds, and has typical values of about 1000 Gauss. Applied fields in this range, and higher, can be achieved with electromagnets using conventional core materials and fairly modest electrical power.

The ferrofluids surrounding the heart are energized by magnetic fields which can originate from electric currents or permanent magnets situated either within or outside the body. For example, the magnetic fields in FIG. 2 are generated by electromagnets 104 and 106 located outside the body. Electromagnets 104 and 106 each include a coil 120 and 122, respectively which is formed, illustratively, of insulated copper wire. Coils 120 and 122 are wound around thin sheets of magnetic material 124 and 126, respectively. The material 124 and 126, in one preferred embodiment, is commercially available under the commercial designation Hiperco, from Carpenter Metals, of Reading, Pa. In the embodiment illustrated in FIG. 2, electromagnets 104 and 106 are generally semi-circular in shape, and are each configured as half torroids set up in a repulsion configuration.

Coils 120 and 122 are coupled to power supply 112 (which in one preferred embodiment is a battery) through switches 108 and 110, which are controlled by controller 114. A bipolar ECG lead 130 is attached at a point on the patient's chest and provides a signal to heart rate sensor 116 which, in turn, provides a signal to controller 114 indicative of the activity of heart 20. Controller 114 controls switches 108 and 110 to selectively energize coils 120 and 122 during systole.

When current is passed through coils 120 and 122, in the direction indicated, a magnetic field is directed through the chest of the patient from the north poles (indicated by the letter N in FIG. 2) to the south poles (indicated by the letter S in FIG. 2) of coils 120 and 122. This field magnetizes the ferrofluid within bag 102 and forces it to a center line (designated by dashed line 132) between electromagnets 104 and 106, in the direction indicated by arrows 134 and 136. Energization of electromagnets 104 and 106 also forces the ferrofluid in bag 102 toward the north and south poles in the direction generally indicated by arrows 138 and 140. Bag 102 reacts in this way because a force develops which pulls the ferrofluid to the point of the strongest field concentration within system 100.

As the field is applied, bag 102, under the force of the ferrofluid driven by the magnetic field, is squeezed inwardly and flattened. The force is proportional to the area of the ferrofluid. Only a few pounds per square inch (psi) are required to pump the blood from within heart 20. This can be achieved when only a few Watts of power are delivered to coils 120 and 122. The amplitude of the coil current controls the pressure exerted by the bag 102 of ferrofluid. Of course, the magnitude of the current can be adjusted until the patient's blood pressure is within a normal range.

In one illustrative embodiment, electromagnets 104 and 106 are contained within a vest worn about the chest of the patient. Also, magnetic shields 142 are provided to cover the region of the gap between the semi-circular magnets, both on the North Pole and South Pole ends, and reside on the outside surface, away from the patient. Magnetic shield 142 confines the high magnetic field to a region within the patient's chest.

Figure 3:
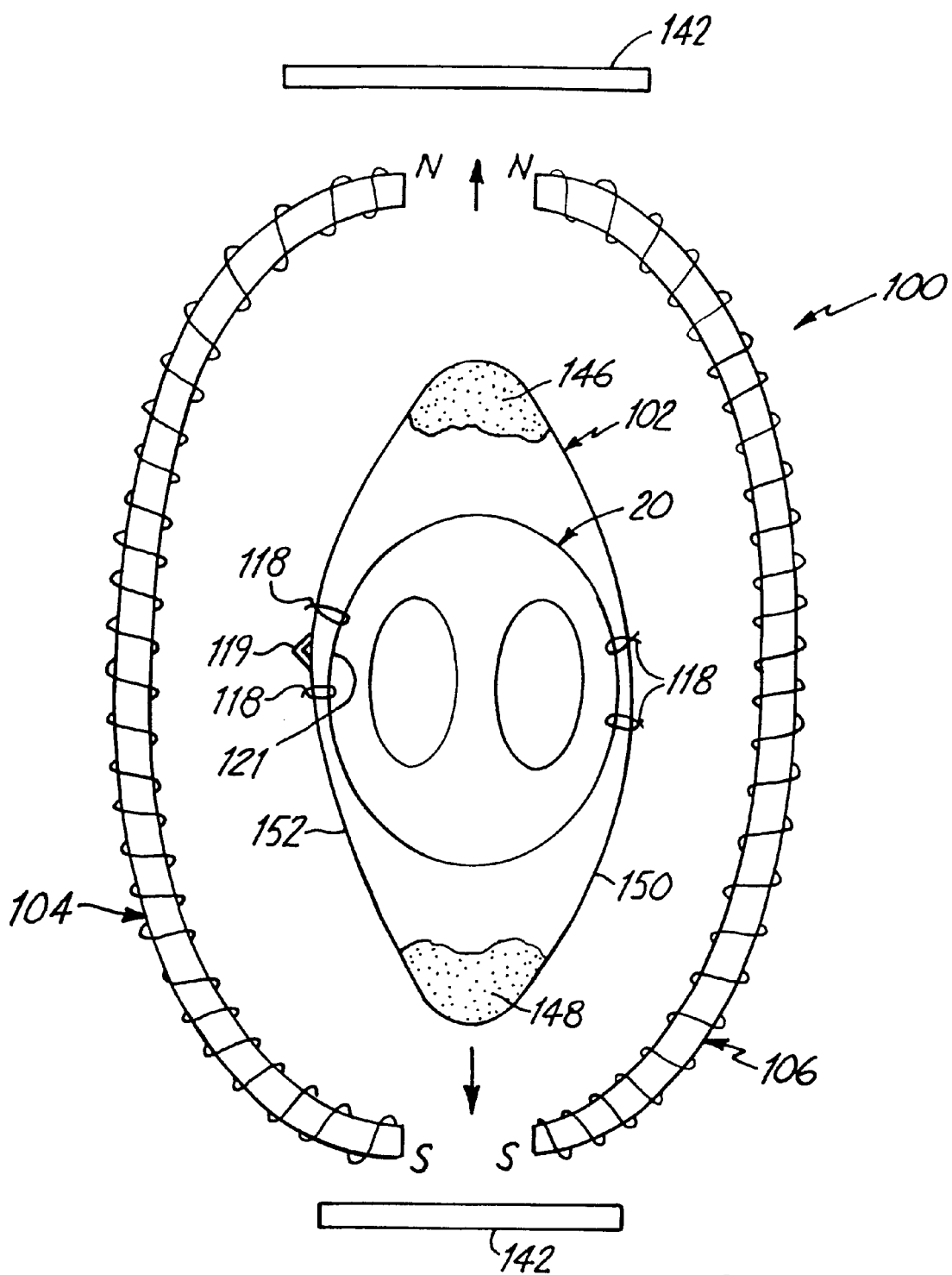
FIG. 3 is a top view of the device shown in FIG. 2.

FIG. 3 is a top view of a portion of system 100 shown in FIG. 2. In FIG. 3, bag 102 is shown as having a pair of generally oppositely disposed pouches 146 and 148 which are connected by bands 150 and 152 which extend about, and are sutured to heart 20. Pouches 146 and 148 contain the ferrofluid material. Thus, when the magnetic field is applied, pouches 146 and 148 are pulled in generally opposite directions toward the north and south poles, respectively. This tends to flatten bag 102 about heart 20. Since pouches 146 and 148 generally reside closer to the north and south poles, this provides more efficient magnetic coupling between those poles and the ferrofluid residing in pouches 146 and 148.

Of course, a wide variety of other bag configurations can be used as well. For example, instead of having two discrete pouches, bag 102 can be formed having a single pocket which extends about the entire periphery of heart 20, bag 102 can be formed having a number of separately divided pockets which extend about the periphery of heart 20. Further, bag 102 may preferably be formed with seams 119 which are disposed about regions having larger coronary vessels 121 in order to avoid compressing those vessels during energization of the coil. Other, different bag configurations can be used as well.

Figure 4A:
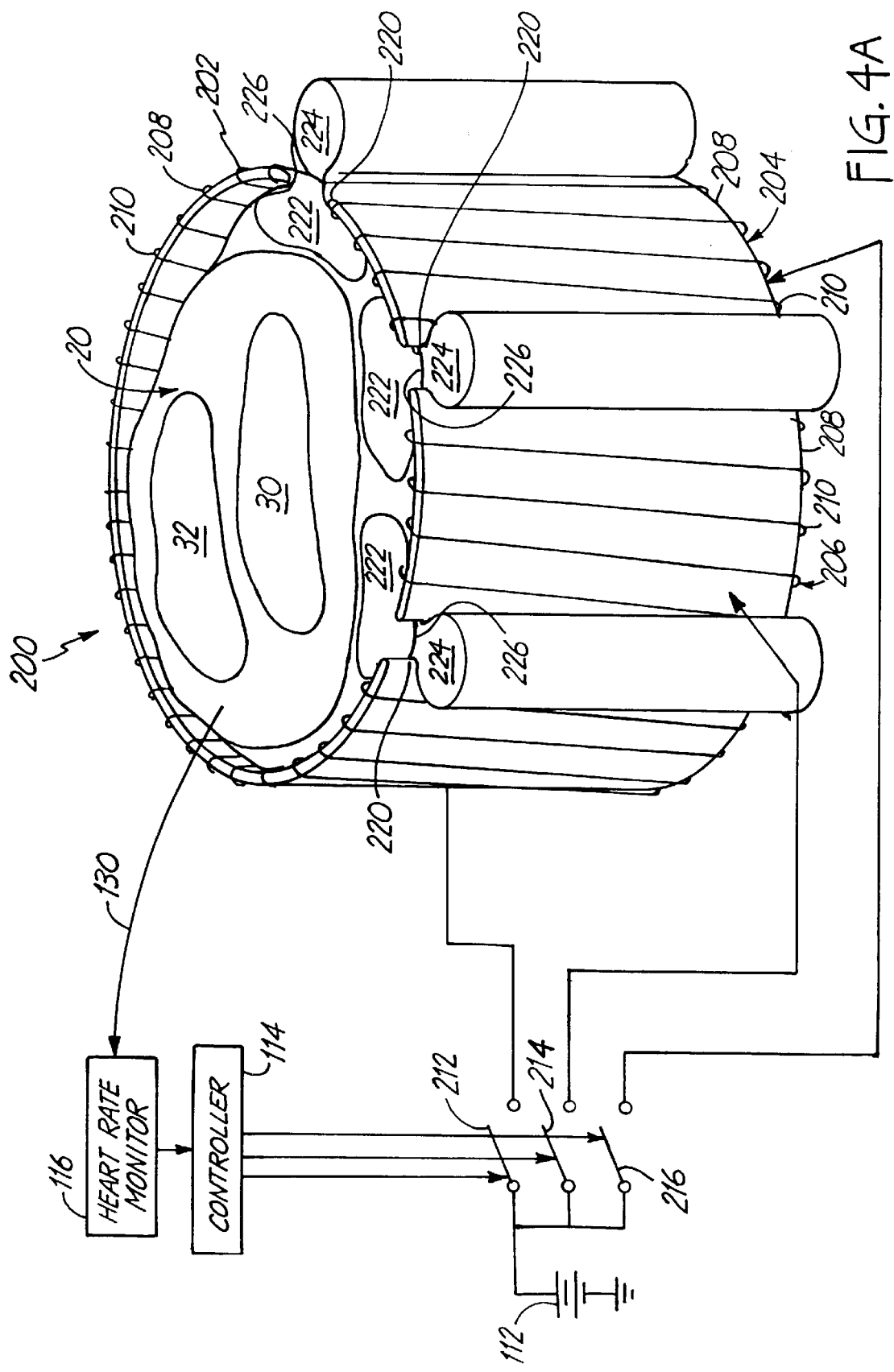
FIGS. 4A–4C illustrate an assist device in accordance with another aspect of the present invention.
Figure 4B:
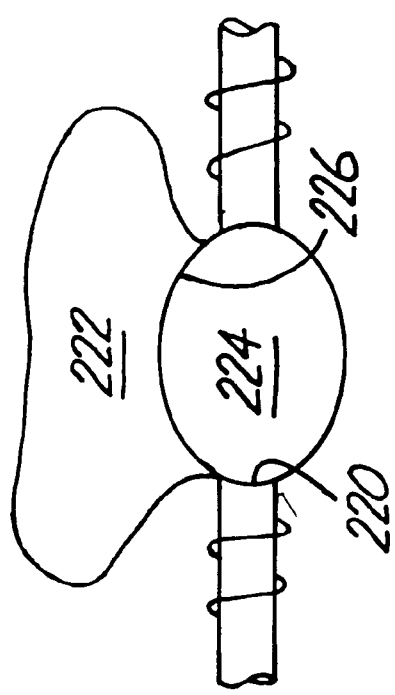
Figure 4C:
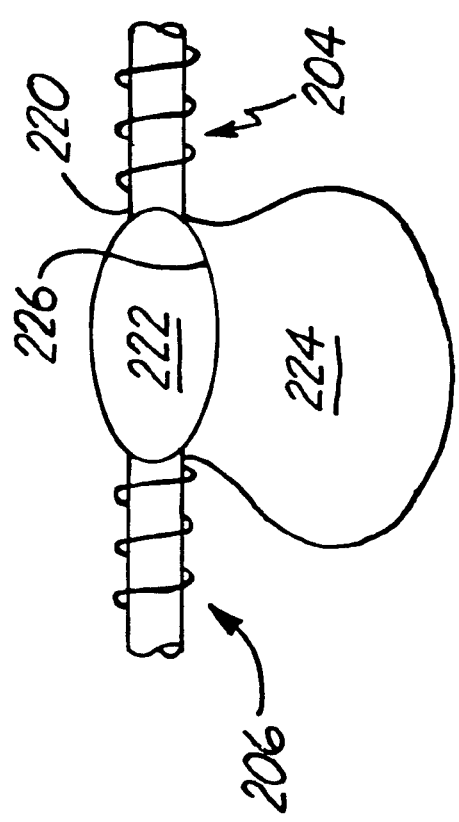

FIGS. 4A–4C illustrate a cardiac assist system 200 in accordance with another aspect of the present invention. A number of other items in system 200 are similar to those in system 100 illustrated in FIGS. 2 and 3, and are similarly numbered. However, system 200 is substantially entirely implantable. System 200 includes a plurality of electromagnets 202, 204, and 206. Each electromagnet includes a core 208 surrounded by a coil 210. Each of the coils 210 is coupled to a corresponding switch 212, 214, or 216, which is controlled by controller 114 based on an ECG or other suitable signal, and selectively couples coils 210 to battery 112. As with system 100, the cores 208 of the electromagnets are preferably a Hiperco or other suitable core material surrounded by coils 210, which is preferably formed of insulated silver or gold wire. All circuitry is preferably implantable, and battery 112 is preferably inductively recharged from outside the body.

The plurality of electromagnets 202, 204 and 206 are separated by gaps 220. Thus, the electromagnets form torroids which substantially surround the heart, but which are split into a plurality of sections which define magnetic gaps 220. Each of the gaps contains two bags 222 and 224, which are separated by a septum 226. In one preferred embodiment, bags 222 are disposed in a direction radially toward the epicardial wall of heart 20, while bags 224 are disposed in an opposite direction.

Bags 222 are filled with non-magnetic fluid, while bags 224 are filled with ferrofluid. When current is applied to the torroidal coils during systole, each ferrofluid bag 224 is drawn into a corresponding gap 220, thus exerting an inwardly directed force on bags 222 and thus on the epicardial wall of heart 20. This force displaces the non-magnetic fluid against the heart wall. During diastole, the coils are de-energized and expansion of heart 20 advances bag 222 back into gaps 220 and thus displaces the ferrofluid in bag 224, out of gap 220. Bags 222 and 224 thus mimic the action of fingers performing heart massage.

In accordance with one aspect of the present invention, gaps 220 are narrower at the apex of heart 20 and wider toward the top of the heart 20. Since the gaps are narrower at the apex, the magnetic field in the narrower gap region is stronger than at the top of heart 20. This causes pressure to build, once the coils are energized, from the apex upward in a natural progression to assist displacement of blood from left ventricle 30. In addition, as illustrated in FIG. 4A, bags 222 and 224 are formed in gaps 220 substantially about the left ventricle 30 of heart 20, while no gaps are preferably defined by the electromagnets about right ventricle 32. This preferentially exerts pressure to assist in displacement of blood from left ventricle 30.

FIGS. 4B and 4C illustrate the action of one set of bags 222 and 224 under the influence of the magnetic field exerted by the electromagnets 204 and 206. It will be appreciated that similar action will take place in each of the gaps 220. FIG. 4B illustrates that the coils on electromagnets 204 and 206 are energized during systole to create a magnetic field in gap 220. The magnetic field draws the ferrofluid in bag 224 into the gap, thus displacing the non-magnetic fluid in bag 222 inwardly toward heart 20. By contrast, when the magnets are de-energized during diastole, the heart chambers fill thus exerting a pressure on bag 222 which displaces the ferrofluid in bag 224 from gap 220, radially outwardly, to allow expansion of the heart 20.

Figure 5A:
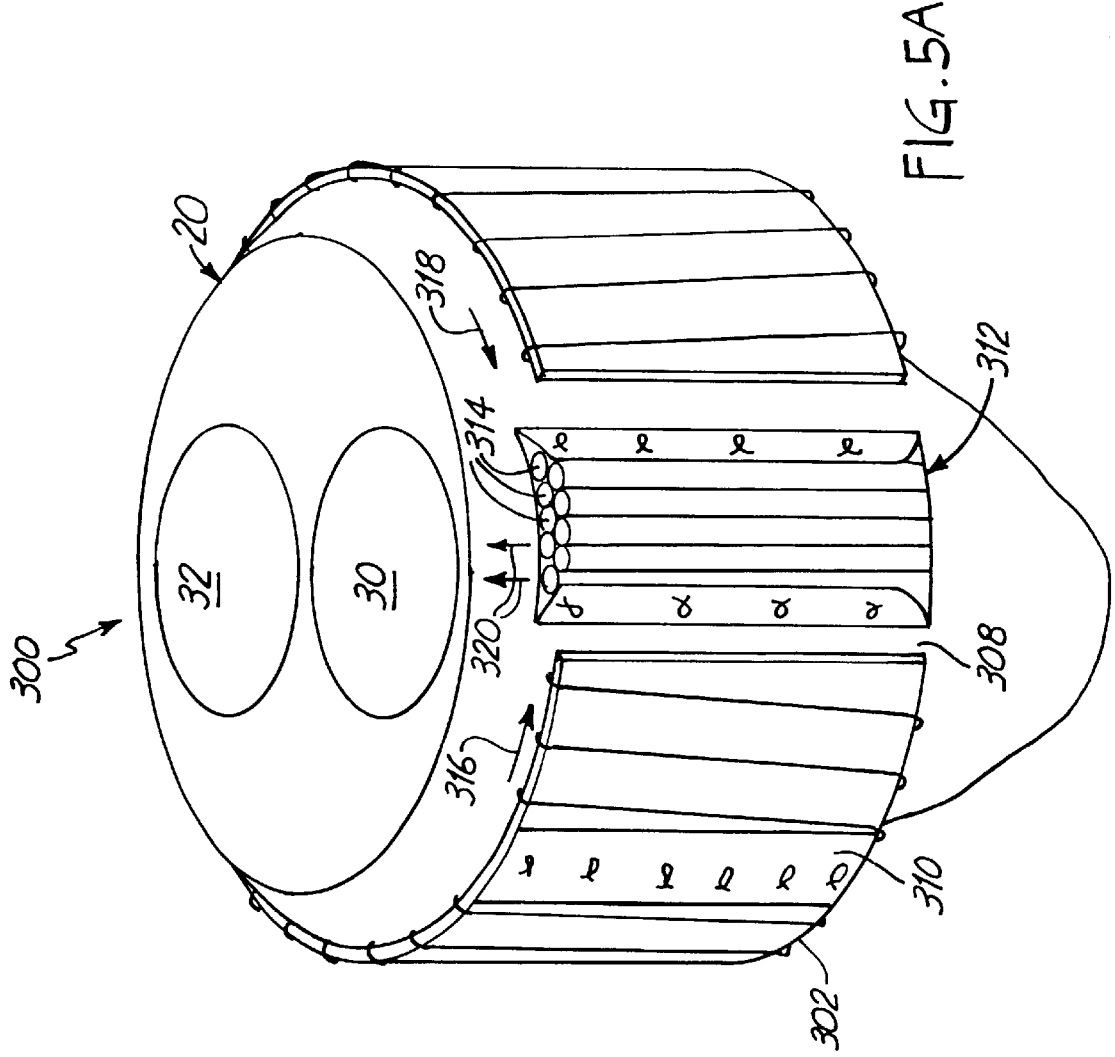

FIGS. 5A–5C illustrate a portion of another assist system 300 in accordance with another aspect of the present invention. As with systems 100 and 200, a heart rate monitor 116, a controller 114, a plurality of switches, and implantable battery 112 are preferably provided in system 300, although they are not illustrated for the sake of clarity. In system 300, a torroidal electromagnet 302 includes a core member 304, which is preferably formed of Hiperco material, and winding 306, which is preferably formed of insulated silver or gold wire. To improve flexibility of the electromagnet, the core may consist of a flat bag of ferrofluid. Core member 304 is disposed about the epicardial layer of heart 20 and defines a gap 308 between ends thereof. Core member 304 is also preferably sutured to heart 300 in two or more locations generally indicated by numeral 310. The areas at which core 304 is sutured to the epicardial wall of heart 20 are preferably proximate left ventricle 30.

System 300 also preferably includes a bag 312 of ferrofluid material. Bag 312 includes a plurality of separate pouches 314, each of which form an elongate finger containing ferrofluid material. Bag 312 is preferably sutured to the epicardial layer of heart 20 in gap 308. The current in coil 306 is preferably driven by an implanted battery, and is switched on during the heart's systolic phase. The beginning of systole can be sensed in several different ways, including by using the QRS complex on an ECG electrode planted on the heart, by using the heart sound produced when the aortic valve opens and sensed by an implanted microphone, or by using a preset pressure threshold as measured on or in the left ventricle. The current through coil 306 is switched off when the T-wave of the ECG signal is identified, when the aortic valve is heard closing, or when the pressure drops below a valve closing threshold.

When coil 306 is energized, the end portions of core 304 tend to move toward one another in the directions generally indicated by arrows 316 and 318, in order to close gap 308. This causes a squeezing on heart 20 in the direction indicated by arrows 316 and 318.

In addition, pouches 314, containing ferrofluid, are preferably centered longitudinally in gap 308, but are radially displaced on the left ventricle 30 outward from the plane of gap 308 when not under the influence of a magnetic field. The ferrofluid in pouches 314 is positioned to partially close the magnetic circuit in gap 308. Thus, when coil 306 is energized, the ferrofluid is drawn radially inward, in the direction indicated by arrows 320, as gap 308 is closing generally tangentially. Thus, left ventricle 30 is receiving a squeezing force in two directions, which enhances the efficiency of the cardiac assist.

It should also be noted that sutures 310 are preferably formed in a region of left ventricle 30, or approximately on a line dividing left ventricle 30 from right ventricle 32. Thus, only left ventricle 30 is squeezed. The sutures maintain a gap between electromagnet 302 and the epicardial wall of heart 20 in the area of right ventricle 32. Thus, right ventricle 32 does not receive any of the squeezing force. Of course, without sutures 310, both left ventricle 30 and right ventricle 32 could be squeezed.

FIGS. 5B and 5C are top views of system 300 illustrating the operation thereof. In FIG. 5B, coil 306 is de-energized, such that gap 308 is larger and pouches 314 are radially displaced, somewhat, from gap 308. However, upon energization of coil 306, gap 308 tends to close in the direction indicated by arrows 316 and 318, and pouches 314 tend to move radially inwardly, into gap 308, in the direction indicated by arrows 320. FIG. 5C illustrates system 300 after coil 306 is energized. Note that gap 308 has closed somewhat, and pouches 314 are now more closely drawn within gap 308, thus squeezing left ventricle 30.

It should be noted that, in FIGS. 5A–5C, and in accordance with one aspect of the present invention, core 304 is made from a plane of individual Hiperco wires overwound with AWG #25 copper wire. This entire structure is only approximately 0.048 inches thick, and is quite flexible, especially when held together by a flexible adhesive, such as urethane. The structure is wrapped around heart 20, and sutured. The ends defining gap 308 are softened with a urethane coating. Flexibility can also be achieved by making the magnetic core from a flat bag of ferrofluid. Alternatively, the torroid is made of a more rigid structure which is shaped to fit snugly about heart 20, without sutures. In such an embodiment, only the magnetically permeable material in bag 312 moves under the influence of the magnetic force, while the ends of the torroid do not close.

Also, in the embodiment shown in FIGS. 5A–5C, the coil resistance of the torroidal coil is approximately 6.5 ohms with a maximum current rating of 1 amp. The average heat dissipation required to generate desirable compressive force is approximately 3.3 watts, with an efficiency of 55% (i.e., 4 watts of pumping power).

Figure 6A:
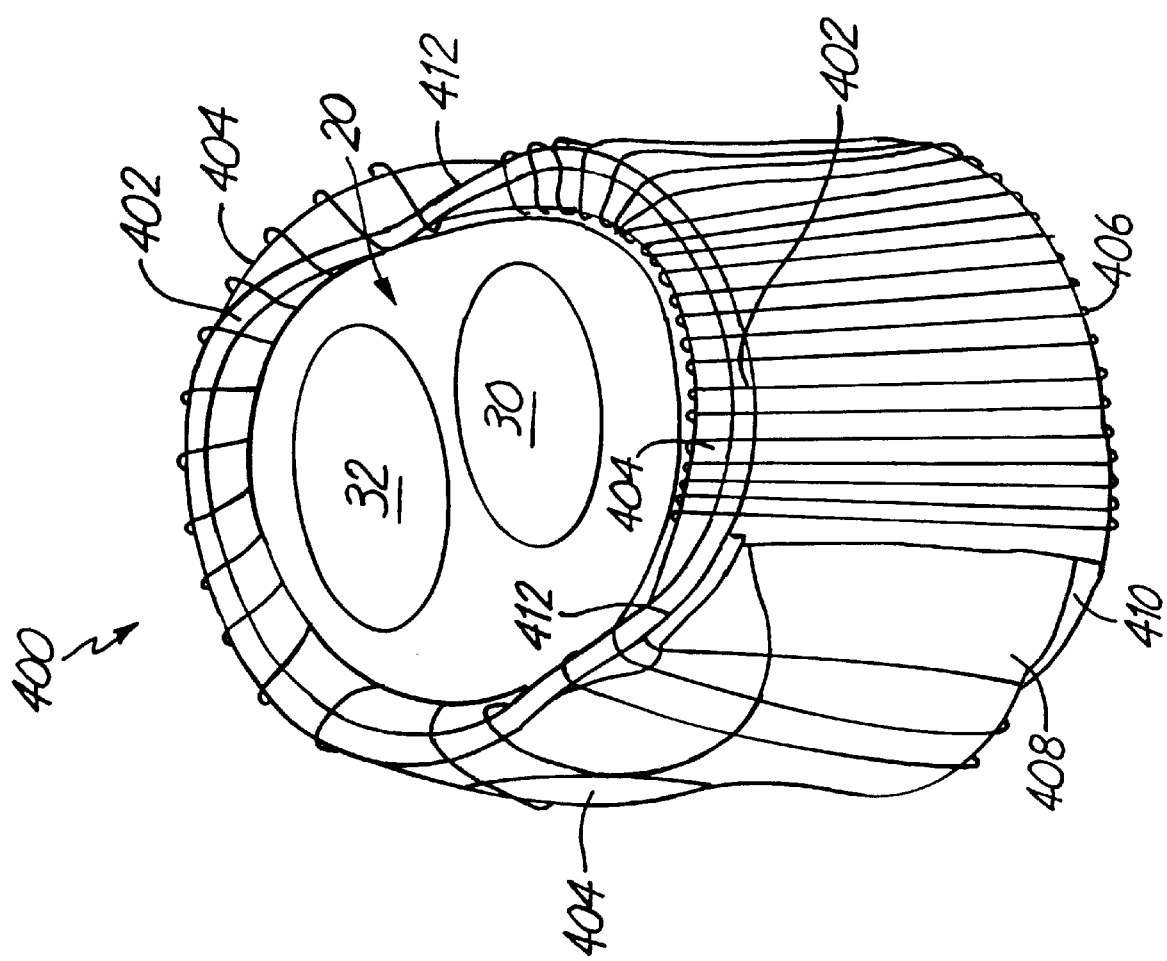
Figure 6B:
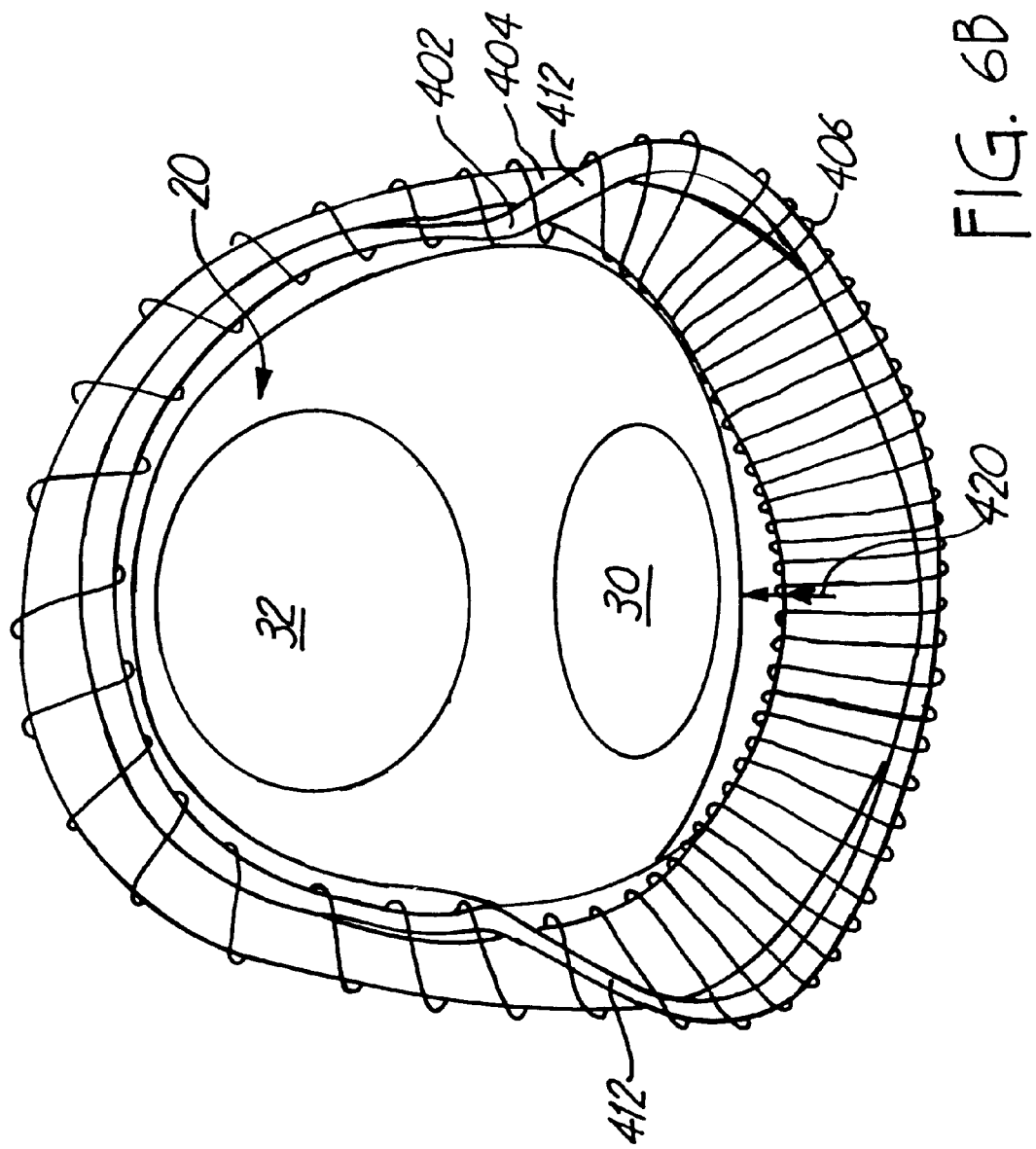

FIGS. 6A–6C illustrate another system 400 in accordance with another aspect of the present invention. System 400 includes a rigid structure or frame 402, which has a bag 404 partially filled with ferrofluid material, supported thereby. In one embodiment, bag 404 is adhered to structural frame 402. The structural frame 402 is formed of non-magnetic material, such as structural plastic, and structure 402 and bag 404 are overwound with a copper coil 406.

The density of the windings is greater in a region proximate left ventricle 30 than in the region proximate right ventricle 32. In one preferred embodiment, the density in the region of left ventricle 30 is double that in the region of right ventricle 32. For example, in a region of structure 402 proximate right ventricle 32, coil 406 includes N windings per unit length. However, in a region of structure 402 proximate left ventricle 30, coil 406 includes more windings, such as 2N windings. It should also be noted that bag 404 is disposed on the outside of rigid structure 402 in the area proximate right ventricle 32, but is disposed on the inside surface of structure 402 in the area proximate left ventricle 30. In accordance with one aspect of the present invention, structure 402 includes a transition section 408 which forms a gap between two longitudinally separated rails 410 and 412. The bag passes from the outer surface of structure 402 to the inner surface thereof through gap 408.

The conductive windings, in one embodiment, are physically attached to the surface of bag 404, and the wires are quite flexible. In another embodiment, where the wires are more rigid, the wires are not attached to the surface of balloon 404, but are instead simply draped over the surface of bag 404. Further, in addition, the windings of coil 406 are physically attached to the outside of structure 402 in the area proximate left ventricle 30, and are physically attached to the inside of structure 402 in the area proximate right ventricle 32.

As with previous embodiments, one or more switches are provided to alternately couple coil 406 to a power supply 112 under the control of a controller 114. In addition, a heart rate sensor 116 can also be provided to provide an input to the control circuitry such that the coil can be energized in synchronicity with the heart action.

Initially, balloon 404 is evacuated and partially re-filled with ferrofluid. When coil 406 is energized, the ferrofluid is forcibly moved within balloon 404 to the region around left ventricle 30, because the greater density of windings in coil 406 in that region produces a stronger magnetic field. This preferentially fills balloon 404 proximate left ventricle 30 and thereby exerts a compression force on the epicardial surface of heart 20 in the region of left ventricle 30. However, even when the coil is energized, there is still enough ferrofluid in the remainder of balloon 404 in the region around right ventricle 32 to complete the torroidal magnetic circuit throughout the entire circumference of heart 20.

During diastole, the left ventricle 30 expands, and coil 406 is de-energized. The ferrofluid within balloon 404 is thus displaced from the left ventricle side of balloon 404 to the right ventricle side of balloon 404 where it occupies space outside of the volume of heart 20. When the right ventricle side of balloon 404 is fully inflated, there is still enough ferrofluid left on the left ventricle side of balloon 404 to make a complete magnetic circuit, once coil 406 is re-energized.

FIGS. 6B and 6C are top views of system 400 shown in FIG. 6A. In FIG. 6B, system 400 is shown with coil 406 energized during systole. It can be seen that balloon 404 preferentially fills on the side of heart 20 proximate left ventricle 30, to exert compressive force in the direction generally indicated by arrow 420 on the epicardial surface of heart 20. However, during diastole, and as shown in FIG. 6C, left ventricle 30 fills thus displacing ferrofluid from the left ventricle side of bag 404, causing it to be displaced to a position outside structure 402 to the right ventricle side of balloon 404.

It should also be noted that, system 400 shown in FIGS. 6A–6C can be sutured to the epicardial surface of heart 20 at any desirable location. For example, structure 402 can be sutured to a region of epicardial surface of heart 20 proximate the division between left ventricle 30 and right ventricle 32. In this way, as balloon 404 fills, it exerts a backpressure on the rigid structure causing balloon 404 to expand inwardly and thus compress left ventricle 30, without exerting any pressure on right ventricle 32. In addition, during diastole, the ferrofluid falls under the force of gravity to the region of balloon 404 proximate the apex of the heart, and to the lower, posterior side of the heart, which is tilted back in the chest cavity. When current is applied to coil 406, the apex region of the heart will be squeezed first, forcing the blood up and out of the heart in a natural contractile motion.

Thus, it can be seen that the present invention provides significant advantages over prior systems. The present invention need not be as compatible and deal with thrombus formation issues as required by systems which are deployed within the heart. Similarly, the present invention does not require external fluid sources for selectively filling a bag or pouch with fluid in order to exert compression on the heart. In addition, the present invention does not deal with natural muscle fibers wrapped around the heart, and thus does not encounter the difficulties associated with such techniques. Also, the present invention exerts a pressure on the heart with a pliable fluid filled surface which yields an atraumatic compressive force on the heart, as opposed to a traumatic compressive force encountered during compression with a rigid mechanical structure.

Although the present invention has been described with reference to preferred embodiments, workers skilled in the art will recognize that changes may be made in form and detail without departing from the spirit and scope of the invention.

What is claimed is:

1. A cardiac assist device for assisting function of a heart, comprising:
    a compressor disposed proximate an epicardial wall of the heart;
    a magnetic field generator comprising an electromagnet, the electromagnet having a core defining a gap and an energizable coil disposed about the core, the field generator configured to selectively generate a field; and
    a ferrofluid operably coupled to the compressor and positioned to be driven, in response to generation of the field, to a compressor position in which the ferrofluid drives the compressor to exert pressure on the heart.

2. The device of claim 1 wherein the ferrofluid is disposed proximate the gap to be driven to the compressor position by generation of the magnetic field in the gap.

3. The device of claim 2 wherein the compressor comprises:
    first and second containment regions disposed on generally opposite sides of the heart, each containment region containing ferrofluid; and
    a pair of compression portions coupled to the first and second containment regions and disposed on generally opposite sides of the heart.

4. The device of claim 3 wherein the electromagnet includes:
    first and second electromagnets having first and second core portions with corresponding first and second coils, the first and second electromagnets being disposed with north poles and south poles thereof generally in alignment, and separated from one another to form the gap.

5. The device of claim 4 wherein the first and second containment regions are configured to be drawn toward the north and south poles, respectively, in response to energization of the first and second electromagnets, such that the compression portions exert a compressive force on the heart.

6. The device of claim 5 wherein the first and second electromagnets are external to a body containing the heart.

7. The device of claim 3 wherein the pair of compression portions are fixedly connected to the heart.

8. The device of claim 2 wherein the electromagnet comprises an implantable core portion disposed about the heart and a coil portion wound about the core portion, the core portion defining a gap, and wherein the compressor comprises:
    a first container containing a nonmagnetic fluid and coupled to the core proximate the gap; and
    a second container containing the ferrofluid and coupled to the core proximate the gap and radially displaced further from the heart than the first container.

9. The device of claim 8 wherein the first and second containers are configured such that when the electromagnet is de-energized, normal heart action drives the first container radially outwardly, substantially displacing the second container from the gap, and wherein energization of the electromagnet drives the second container into the gap, substantially displacing the first container from the gap exerting pressure on the heart.

10. The device of claim 2 wherein the gap is generally aligned with a longitudinal axis of the heart and is narrower at a portion thereof proximate an apex of the heart than at a longitudinally upper portion thereof.

11. The device of claim 9 wherein the electromagnet includes a plurality of core portions each with a corresponding coil, the plurality of core portions defining a plurality of gaps, each gap having one of the first containers and the second containers positioned proximate thereto.

12. The device of claim 2 wherein the electromagnet is implantable and coupled to the heart and wherein the compressor comprises a container containing the ferrofluid coupled to the heart and disposed proximate the gap such that energization of the coil draws the container radially within the gap to exert a compressive force on the heart.

13. The device of claim 12 wherein the electromagnet is coupled to the heart such that the gap is proximate the left ventricle and such that the core is radially separated from the heart in an area proximate the right ventricle.

14. The device of claim 2 wherein the compressor comprises:
    a plurality of containment regions disposed about the heart, each containment region containing ferrofluid.

15. The device of claim 14 wherein the plurality of containment regions are generally aligned with a longitudial axis of the heart.

16. The device of claim 2 wherein the compressor is adapted to drive the ferrofluid away from the heart to the compressor position.

17. A cardiac assist device for assisting function of a heart, comprising:
    a compressor disposed proximate an epicardial wall of the heart;
    a monitor configured to detect a rhythm of the heart;
    a field generator coupled to the monitor and configured to selectively generate a field based on the rhythm detected by the monitor; and
    a fluid operably coupled to the compressor and positioned to be driven, in response to generation of the field, to a compressor position in which the fluid drives the compressor to exert pressure on the heart.

18. A cardiac assist device for assisting function of a heart, comprising:
    a compressor disposed proximate an epicardial wall of the heart;
    a field generator configured to selectively generate a field of variable strengths, varying about a periphery of the heart; and
    a fluid operably coupled to the compressor and positioned to be driven, in response to generation of the field, to a compressor position in which the fluid drives the compressor to exert pressure on a side of the heart in accordance with the field strength.

19. A cardiac assist device for assisting function of a heart, comprising:
    a compressor disposed proximate an epicardial wall of the heart;
    a field generator comprising an electromagnet having a core and an energizable coil disposed thereabout configured to selectively generate a field; and
    a ferrofluid arranged to act as the core and operably coupled to the compressor and positioned to be driven, in response to generation of the field, to a compressor position in which the ferrofluid drives the compressor to exert pressure on the heart.

20. A cardiac assist device for assisting function of a heart, comprising:
- a compressor disposed proximate an epicardial wall of the heart;
- an electric field generator configured to selectively generate a field; and
- a dielectric fluid operably coupled to the compressor and, positioned to be driven, in response to generation of the field, to a compressor position in which the fluid drives the compressor to exert pressure on the heart.

21. A cardiac assist device for assisting function of a heart, comprising:
- a compressor disposed proximate an epicardial wall of the heart;
- a magnetic field generator configured to selectively generate a magnetic field, the magnetic field generator comprising:
  - a structural support disposed about the heart;
  - a container coupled to the structural support; and
  - a coil disposed about the container and coupled to the structural support; and
- a ferrofluid contained in the container operably coupled to the compressor and positioned to be driven, in response to generation of the field, to a compressor position in which the ferrofluid drives the compressor to exert pressure on the heart.

22. The device of claim 12 wherein the container is disposed radially outside the structural support in a region proximate the right ventricle.

23. The device of claim 21 wherein the container is disposed radially inside the structural support in a region proximate the left ventricle.

24. The device of claim 21 wherein the coil is configured to, when energized, generate a magnetic field which preferentially draws the ferrofluid to a portion of the container proximate the left ventricle.

25. The device of claim 24 wherein the coil has a winding density which is higher in a region proximate the left ventricle than in a region proximate the right ventricle.

* * * * *